(12) United States Patent
Kovács-Vajna

(10) Patent No.: US 6,236,741 B1
(45) Date of Patent: *May 22, 2001

(54) METHOD AND DEVICE FOR IDENTIFYING FINGERPRINTS

(75) Inventor: Zsolt Kovács-Vajna, Bologna (IT)

(73) Assignee: STMicroelectronics S.r.l., Agrate Brianza (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/802,658

(22) Filed: Feb. 19, 1997

(30) Foreign Application Priority Data

Feb. 22, 1996 (EP) .................................................. 96830080

(51) Int. Cl.[7] ...................................................... G06K 9/00
(52) U.S. Cl. ........................................... 382/125; 340/5.53
(58) Field of Search ..................................... 382/124, 125, 382/209; 340/5.3, 5.31, 5.52, 5.53

(56) References Cited

U.S. PATENT DOCUMENTS

| 4,641,350 | 2/1987 | Bunn ..................... 382/124 |
| 5,493,621 | * 2/1996 | Matsumura ........................ 382/125 |
| 5,613,014 | * 3/1997 | Eshera et al. ......................... 382/125 |
| 5,659,626 | 8/1997 | Ort et al. .............................. 382/125 |
| 5,825,907 | 10/1998 | Russo ................................... 382/124 |
| 5,841,888 | 11/1998 | Setlak et al. ......................... 382/124 |
| 5,845,005 | 12/1998 | Setlak et al. ......................... 382/124 |

FOREIGN PATENT DOCUMENTS 0 343 580   11/1989   (EP) .

OTHER PUBLICATIONS

Elliott, *Parallel Processing: State of The Art Report*, Pergamon Infotech, Maidenhead, Berkshire, 1987, Chap. I, "Automatic Fingerprint Recognition," (ed. C.R. Jesshoppe), pp. 3–17.

Fukue et al., "Fingerpirnt Verification System—Verification Algorithm," *IEEE TENCON* 87, Seoul 1987, pp. 71–75.

Kramer, A. et al., *Flash–Based Programmable Nonlinear Capacitor for Switched–Capacitor Impelementions of Neural Networks*, IEDM, 1994, pp. 449–452.

Yahagi, Hironori et al., *Moving–Window Algorithm for Fast Fingerprint Verification*, Southeastcon '90 Proceedings, vol. 1, New Orleans, Louisiana, 1990, pp. 343–347.

* cited by examiner

Primary Examiner—Amelia M. Au
Assistant Examiner—Samir Ahmed
(74) Attorney, Agent, or Firm—Theodore E. Galanthay; Robert Iannucci; Seed IP Law Group, PLLC

(57) ABSTRACT

A method of identifying fingerprints, the method including the steps of: acquiring a test image formed by a number of test points characterized by different grey levels defining a test surface; determining significant points in the test image; and verifying the similarity between regions surrounding the significant points and corresponding regions of a reference image whose points present different grey levels defining a reference surface. The similarity between the regions is verified by computing the integral norm of portions of the test and reference surfaces; and the integral norm is computed using flash cells programmed with a threshold value correlated to the value of the grey levels in the reference region, by biasing the flash cells with a voltage value correlated to the grey level in the test region, and measuring the charge flowing through the flash cells.

14 Claims, 5 Drawing Sheets

METHOD AND DEVICE FOR IDENTIFYING FINGERPRINTS

TECHNICAL FIELD

The present invention relates to a method and device for identifying fingerprints.

BACKGROUND OF THE INVENTION

As is known, the fact that no two fingerprints are alike and therefore represent a sort of identity card results in a wide range of applications. For example, in addition to being traditionally used in crime detection, it has also been suggested to use fingerprints as a sort of personal key or signature to improve the safety of credit cards and control access to security areas, computers or banking systems, and also as a substitute for cumbersome house or car keys.

The difficulty in identifying fingerprints lies in defining a score assignable to a pair of fingerprint images and expressing the likelihood that both belong to the same person. Moreover, the two fingerprints for comparison are acquired at different times, one normally forming part of a data bank containing references to known persons, and the other being validated or identified by comparison with the first.

Traditional fingerprint identification methods, which are normally performed manually by experts, comprise numerous classification steps. In recent times, however, automatic methods have been proposed, some of which comprise preclassification steps similar to those of traditional methods, while others dispense entirely with such steps and, commencing directly from the fingerprint image obtained, for example, by means of a scanner or sensor, provide for identification by appropriate processing. The present invention relates to the second type of approach.

A fully automatic identification system is described, for example, in "Automatic Fingerprint Identification" by K. Asai, Y. Kato, Y. Hoshino and K. Kiji, Proceedings of the Society of Photo-Optical Instrumentation Engineers, vol. 182, Imaging Applications for Automated Industrial Inspection and Assembly, p. 49–56, 1979. According to this system, the significant points in the image (epidermal ridge terminations and bifurcations, known as "minutiae") are determined directly from the image in tones of grey, and matching of the prints is determined on the basis of a ridge count and the direction of the minutiae, as in the manual method.

In "Fingerprint Identification using Graph Matching" by D. K. Isenor and S. G. Zaky, Pattern Recognition, vol. 19, no. 2, p. 113–122, 1986, a graph matching method is presented whereby the epidermal ridges and grooves are located in the print image, the ridges being numbered and oriented, and the grooves forming the background; a degree of adjacency is defined indicating which ridge is adjacent to which other; any irregularities due to soiling or interrupted ridges due to the acquisition system are identified and corrected on the graph to obtain a final graph representing the print in coded form; and the similarity of the prints is determined by comparing the graphs.

In "Automated Fingerprint Identification by Minutia-network Feature-Matching Processes" by K. Asai, Y. Hoshino and K. Kiji, Transaction of the Institute of Electronics, Information and Communication Engineers D-II, vol. J72D-II, no. 5, p. 733–740, May 1989 (in Japanese), use is made of a minutia-network containing termination and bifurcation points, and the epidermal ridges are counted to relate the significant adjacent points. The local direction of the epidermal ridges is also taken into consideration, and the pairs of matching points are obtained by coordinate transformation and similarity computation.

Assessed using a few hundred known prints, the above systems do not yet provide for the degree of accuracy required for police work involving the comparison of millions of images.

SUMMARY OF THE INVENTION

It is an object of the present invention to provide an identification method and device affording a high degree of reliability—such as to minimize erroneous positive identifications or nonidentification—and rapid response time.

A preferred embodiment of the invention is directed to a device and method for identifying fingerprints. The method acquires a test image formed by a number of test points characterized by different grey levels defining a test surface. The method determines significant points in the test image and verifies the similarity between regions surrounding the significant points and corresponding regions of a reference image whose points present different grey levels defining a reference surface. The similarity between the regions is verified by computing the integral norm of portions of the test and reference surfaces. Preferably, the integral norm is computed using flash cells programmed with a threshold value correlated to the value of the grey levels in the reference region, by biasing the flash cells with a voltage value correlated to the grey level in the test region.

DETAILED DESCRIPTION OF THE INVENTION

Figure 1:
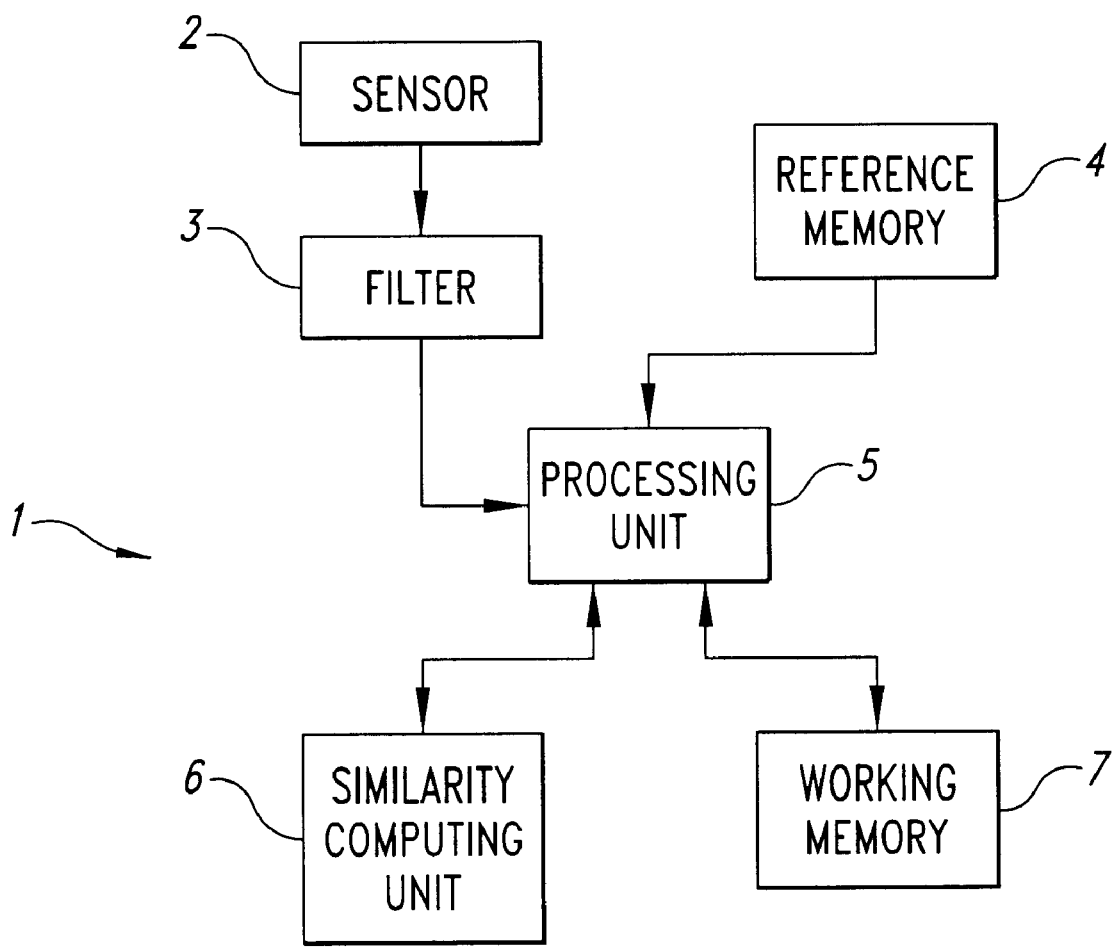
FIG. 1 shows a block diagram of a fingerprint identification device according to the present invention.

FIG. 1 shows a fingerprint identification device 1 that includes a sensor 2 for acquiring fingerprint images in the form of an array of dots characterized by different grey levels. A filter 3, connected to the sensor 2, filters the images detected by sensor 2. A reference memory 4 contains reference information relative to one or more reference images with which the image detected by sensor 2 is compared. A processing unit 5, connected to the filter 3 and memory 4, compares the filtered image with the reference image/s stored in the reference memory 4. A similarity computing unit 6, connected to processing unit 5, performs predetermined steps in the identification process as described in detail below. The device 1 also includes a work memory 7 connected to processing unit 5.

The sensor 2 operates according to any known principle—e.g., optical, capacitive, piezoelectric, ultrasonic, thermal—to obtain images (test images) of, say, 512×512 dots (pixels). Filter 3, which filters the images supplied by sensor 2, may be formed in various ways, depending on the operating principle of sensor 2, and, in some solutions, may comprise a digital software filter and be implemented directly by processing unit 5. Memory 4, which may also be of any known type, stores information relative to a number of images associated with the application in question (one or a small number of images if the system is used as a personal key, or millions of images if the system is used for crime detection). Such reference information preferably comprises reference print images comprising a number of pixels characterized by different grey levels (like the images detected by sensor 2), as well as information derived by processing the reference print images and for direct or indirect comparison with information derived from the test image, according to the method described below, to reduce the amount of processing required each time to identify a print.

Figure 2:
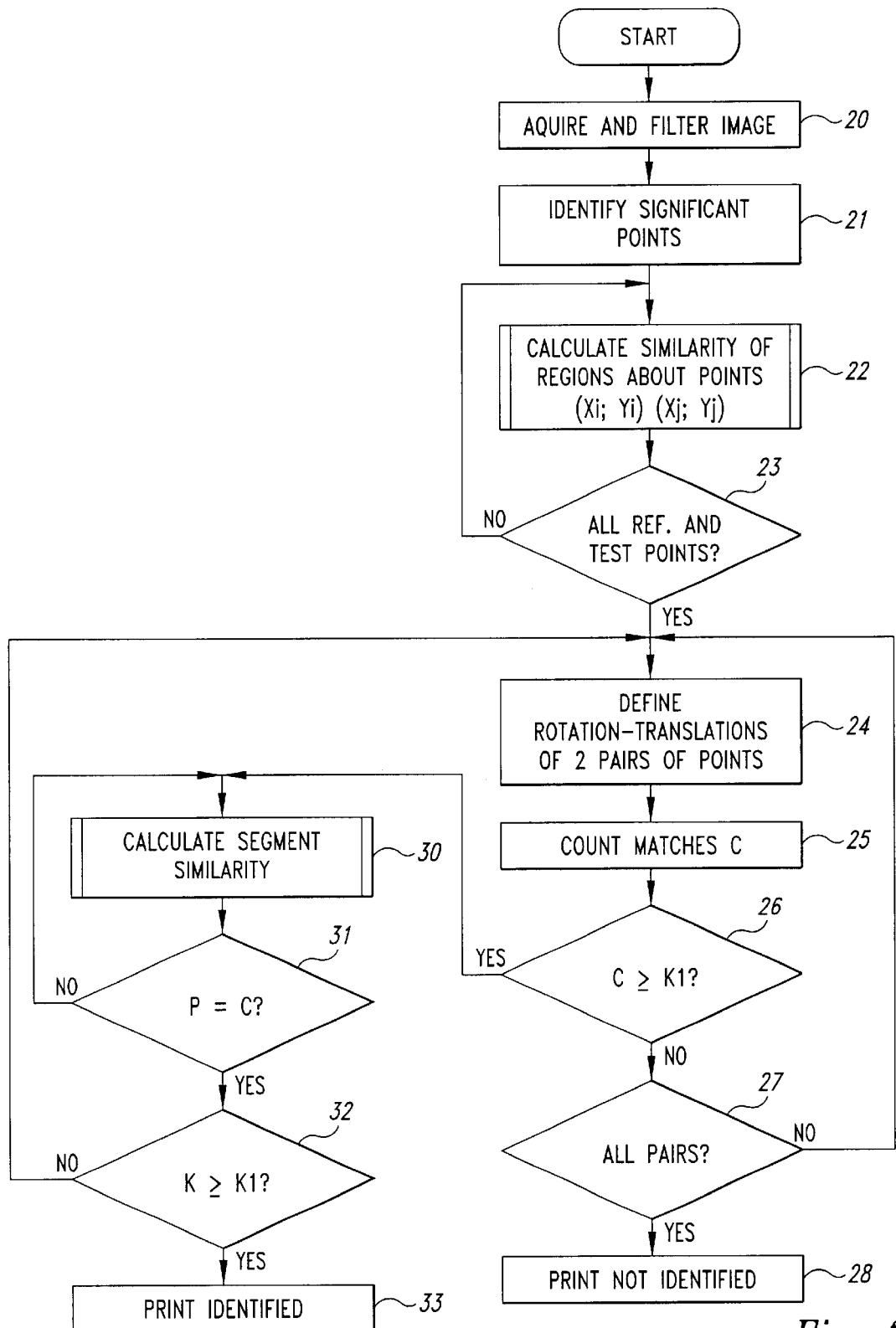
FIG. 2 is a flowchart of a fingerprint identification method according to the present invention.
Figure 4:
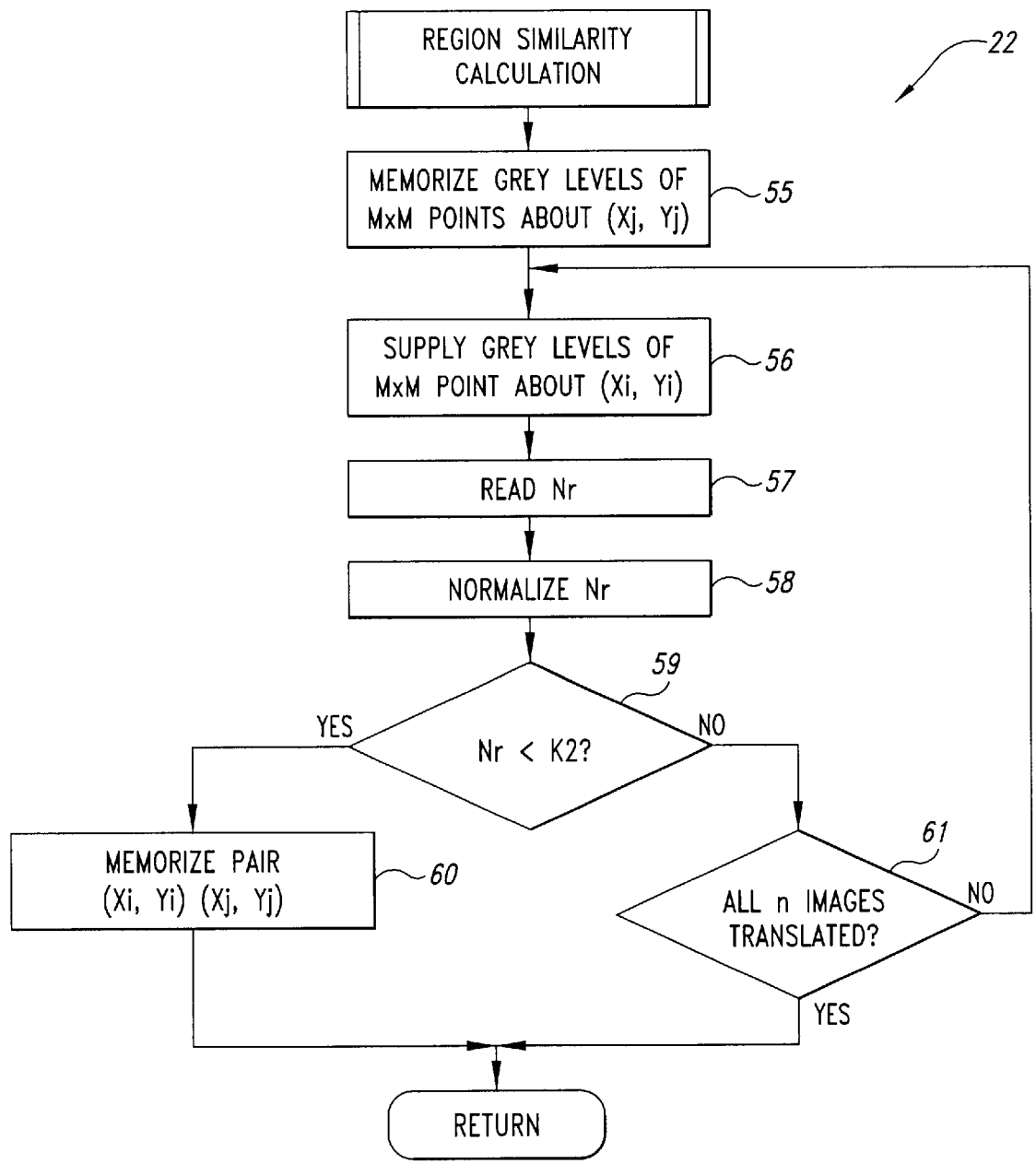
FIG. 4 is a flowchart of the region similarity computation step of the method shown in FIG. 2.
Figure 5:
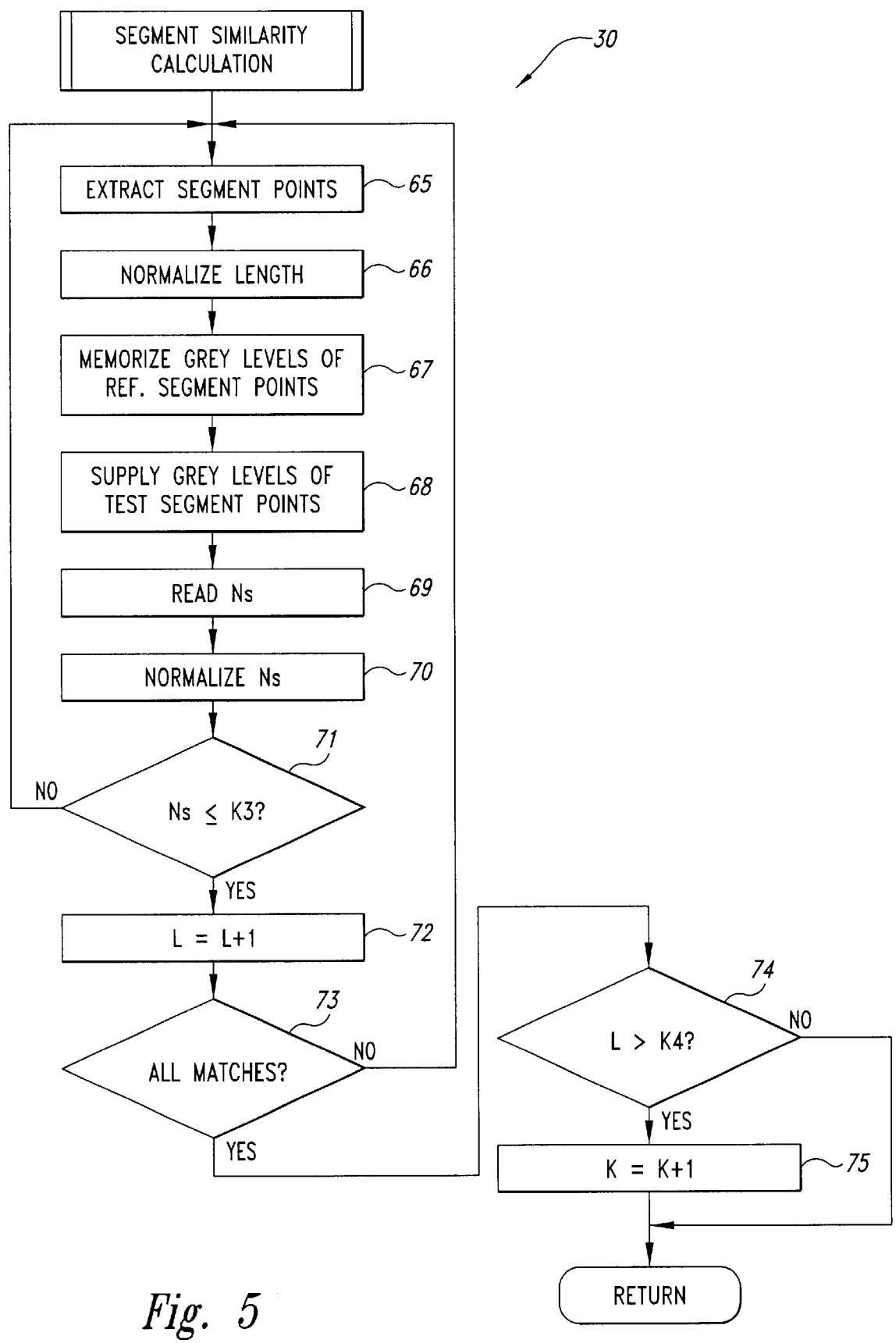
FIG. 5 is a flowchart of the segment similarity computation step of the method shown in FIG. 2.

Device 1 operates as described below with reference to FIGS. 2, 4, and 5 relative to the comparison of a test and reference image.

Obviously, to identify the test image from a number of reference images, the procedure described below is repeated for each reference image.

To begin with, a test image is acquired by sensor 2 and filtered in known manner by filter 3 to obtain as regular an image as possible in tones of grey (step 20). The filtered image, memorized in working memory 7, is processed by processing unit 5 to define the coordinates (Xi,Yi) of significant points represented by the terminations and bifurcations of the epidermal ridges, so called minutiae, (step 21). Such processing to determine the significant points may be performed in any known manner, e.g., as indicated in the above article "Automatic Fingerprint Identification", 1979, by Asai, Kato, Hoshino and Kiji. The resulting significant points are then memorized in working memory 7 and compared by the similarity computing unit 6 with corresponding significant points in the reference image (extracted and memorized beforehand using the same significant point extraction procedure as for the test image). In particular, each significant point in the test image with coordinates (Xi,Yi) is compared with all the significant points in the reference image with coordinates (Xj,Yj) to establish a local similarity between the regions centered about the significant points. The local region similarity check procedure (step 22 in FIG. 2) is shown in the FIG. 4 flow-chart and described in detail later on.

When an actual similarity is determined, the local region similarity check process generates a pair of significant points (one in the test image and one in the reference image) characterized by a local similarity (in terms of grey tones) of the regions surrounding them, and the pairs of significant points are memorized in working memory 7. In step 23, a check is then made to determine whether the local region similarity check has been repeated for all the significant points in the test image. If it has not (NO output of step 23), it is repeated, and, when all the significant points in the image have been checked (YES output of interrogation step 23), a list of pairs of significant points is available.

For each pair of significant points so obtained, a coordinate translation and rotation from the test image to the reference image is defined to match a second pair of significant points within a given tolerance (step 24), so that, for each two pairs of significant points, a linear rotation-translation transformation is identified on which to suppose matching of the print images.

Having identified a rotation-translation as described above, the matching points of the other pairs of significant points are determined (step 25). In other words, applying the defined rotation-translation, a count is made of the significant points in the test image matching the significant points with which they are paired in the reference image. If there are fewer than K1 matches (matching pairs of significant points—NO output of interrogation step 26), assumed matching of the test and reference prints with the current rotation-translation is rejected, and the rotation-translation definition and match count procedure is repeated for another two pairs of significant points, and so on until a rotation-translation resulting in more than the minimum required number of matches is defined (YES output of step 26) or until all the possible transformations have been checked (YES output of step 27), in which latter case, the prints are definitely considered nonmatching, and the test and reference image comparison is terminated negatively (step 28).

Conversely, in the event of at least K1 matching pairs of significant points in the test and reference images, real matching of the prints is determined (step 30) by appropriately comparing image segments connecting a first pair of significant points (one in the test image and one in the reference image) with all the other pairs of significant points, and by validating the first pair of significant points when a sufficient similarity is determined for at least a predetermined number of image segments as defined above. The procedure for defining the similarity of the segments and validating each pair of matching significant points is shown in the FIG. 5 flow-chart and described in detail below.

At this point, a check is made to determine whether the similarity of the segments has been determined for all the matching significant points (step 31). If it has not (NO output of step 31), then step 30 is repeated. If it has (YES output of step 31), a check is made to determine whether the number K of validated matching significant points is greater than or equal to a given threshold, in this case equal to the minimum threshold K1 for a given rotation-translation to be considered valid (interrogation step 32). In the event of a positive response (YES output of step 32), the print is considered identified (step 33); in the event of a negative response (NO output) step 32 goes back to step 24 to determine another rotation-translation.

A description will now be given of the calculation of the similarity of the regions surrounding two significant points, one in the test image with coordinates (Xi,Yi), and one in the reference image with coordinates (Xj,Yj), according to step 22 of FIG. 2.

Using the grey values of the test and reference images, a region M×M (e.g., 16×16) is defined about each test and reference point being compared. According to one aspect of the present invention, the similarity of the regions so defined is determined by calculating the value of the integral norm of two surfaces $Si_t$ and $Sj_r$ defined as:

$$Si_t = \{x,y,z\} : z = \text{grey}(x,y)$$

where $Xi-8 \leq x < Xi+8$; $Yi-8 \leq y < Yi+8$ for the test image points, and $$Sj_r \times \{x,y,z\} : z = \text{grey}(x,y)$$

where $Xj-8 \leq x < Xj+8$; $Yj-8 \leq y < Yj+8$ for the reference image points, and wherein grey(x,y) is the grey tone of the test or reference image at point (x,y).

The integral norm N of two surfaces $Si_t$ and $Sj_r$ equals:

$$N = \iint_{M \times M} |Sj_r(x,y) - Si_t(x,y)| dx dy \qquad (1)$$

Since, in this case, the region M×M and the functions $Si_t$, $Sj_r$ of which to compute the similarity are discrete, the double integral is converted into a double summation, and (1) becomes $$N = \Sigma\Sigma |Sj_r(x-Xi+Xj, y-Yi+Yj) - Si_t(x,y)| \quad (2)$$

where $Xi-8 \leq x < Xi+8$; $Yi-8 \leq y < Yi+8$.

Computing the above norm is particularly onerous in the application in question, which on average involves 100–150 significant points for each test and reference image, and wherein the coordinate of each significant point is definable within a tolerance of about five pixels (±2 in relation to the given coordinate) both horizontally and vertically. This therefore means that, for each pair of significant points for comparison, 25 norms would have to be computed, and the similarity verify step would require 25×T×S calculations as per equation (2) (given T significant points in the test image and S significant points in the reference image). Even reducing the operations required for each pair of significant points to compute the norm in only 9 of the 25 coordinate tolerance points, computing time would still be considerable and unacceptable in many applications.

According to one aspect of the present invention, the above norm is computed using an array of analog flash cells, which is described in detail by A. Kramer, M. Sabatini, R. Canegallo, M. Chinosi, P. L. Rolandi and P. Zabberoni in an article entitled "Flash-Based Programmable Nonlinear Capacitor for Switched-Capacitor Implementations of Neural Networks" in IEDM Tech. Dig. p. 17.6.1–17.6.4, December 1994. The array of analog flash cells may be used to calculate the absolute difference between two values by connecting the source and drain regions of two flash cells to each other and to an input node of a charge integrator, supplying the gate terminal of a first cell with a voltage corresponding to the first value, memorizing in the same first cell, as the threshold voltage, the second value to be subtracted from the first, supplying the gate terminal of the second cell with a voltage complementary to that supplied to the first cell, and memorizing as the threshold voltage in the second cell a value complementary to the second value to be subtracted (see FIG. 3 in the above article). As stated in the article, it is also possible to calculate the sum of the difference between pairs of values by connecting the output nodes of different pairs of cells supplied (as threshold and input voltages) with the pairs of values to be added (see FIG. 4 in the article, relative to calculating the Manhattan distance between two vectors).

Using the same principle, the above norm may be computed by parallel computing all the individual differences between the grey levels of pairs of corresponding points in the test and reference images to obtain the value of the norm directly at the output. One example of a flash cell array for computing the norm defined in equation (2) is shown in FIG. 3 and described below.

Figure 3:
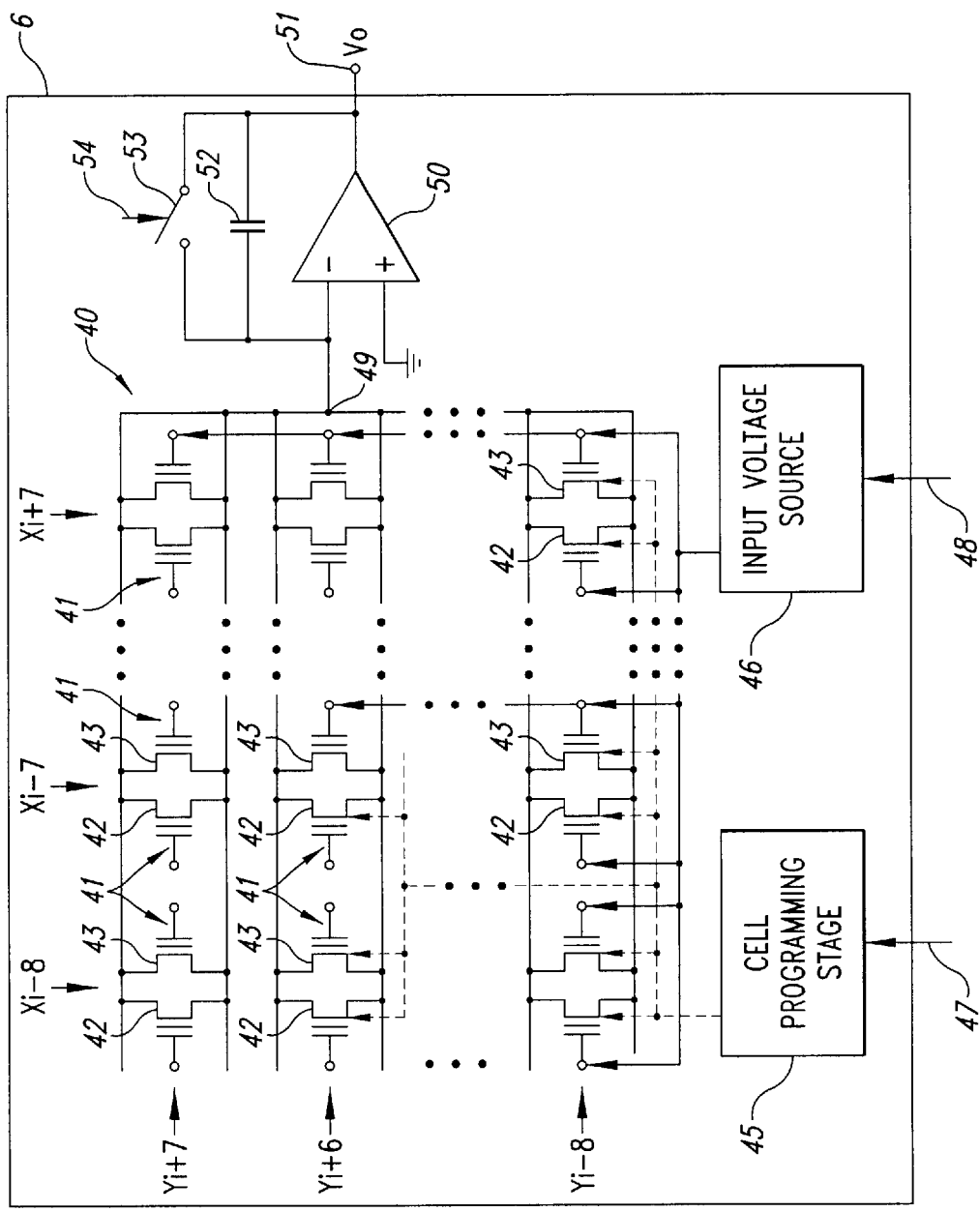
FIG. 3 shows a simplified circuit diagram of a detail in FIG. 1 for performing some of the steps shown in FIGS. 2, 4, and 5.

FIG. 3 shows one possible structure of similarity computing unit 6, which comprises an array 40 of M×M pairs of cells 41 (more specifically, in the case of 16×16 pixel regions, 16×16 pairs of cells are provided) arranged in M rows and M columns, and each corresponding to a pixel of the regions whose similarity is being computed (for the sake of simplicity, the addresses of pairs of cells 41 are therefore indicated using the same x and y coordinates as the pixels in the test image). Each pair of cells 41 comprises a first cell 42 and a second cell 43. Unit 6 also comprises a programming stage 45 connected to pairs of cells 41 and formed in known manner (e.g., as described in EP-A-O 621 603 entitled "Method and circuit for tunnel programming floating-gate MOSFET transistors" filed by the present Applicant); and a voltage source 46 connected to the gate terminals of all of cells 42, 43. Stage 45 and source 46 are controlled by processing unit 5, by which they are supplied with respective grey level values and commands as shown schematically by arrows 47, 48, and are connected to cells 42, 43 by selecting and addressing means (not shown).

The drain and source terminals of all of cells 42, 43 are connected to each other and to a node 49 connected to the inverting input of a charge-integrating operational amplifier 50, which therefore presents a grounded noninverting input and the output 51 connected to the inverted input via a capacitor 52. A reset switch 53 controlled by processing unit 5 (arrow 54) is connected in parallel with capacitor 52; and the output 51 of operational amplifier 50 defines the output of unit 6, and is connected to processing unit 5 to supply a voltage $V_o$.

For each pair of cells 41, therefore, cell 42 is programmed by stage 45 with a first voltage proportional to the grey level of the corresponding pixel in the reference image, and the corresponding cell 43 is programmed with a voltage complementary to the first programming voltage, according to the equation indicated in FIG. 3 of the above article. For all the pairs of cells 41, voltage source 46 then supplies the input of cell 42 with a second voltage proportional to the grey level of the corresponding pixel in the test image, and the input of cell 43 with a voltage complementary to the second voltage, so that the voltage $V_o$ at output 51 of unit 6 is proportional to the sum of the difference in the grey levels of corresponding pixels in the test and reference images.

Given the above, the manner in which the similarity of given regions is computed will now be described with reference to FIG. 4. Given a predetermined position of the significant point within the tolerance region and the respective corresponding region M×M in the test image, the grey levels of the pixels in a region M×M surrounding a significant point in the reference image are memorized as programming levels in matrix 40 (step 55); the inputs of matrix 40 are supplied, as described above, with voltages correlated to the grey levels of corresponding pixels in said region M×M in the test image (step 56); the output voltage $V_o$ equal to the value of the integral norm $N_r$ computed for region M×M is acquired (step 57); said value is normalized (e.g. so that it is between 0 and 1) to eliminate the effects of any differences in contrast between different images (step 58); and the normalized norm value is then compared (step 59) with a maximum threshold K2 (e.g., 0.2). In the event the normalized norm value is below the threshold (strong grey tone similarity of the compared test and reference image regions—YES output of step 59), the pair of significant points with coordinates (Xi,Yi) in the test image and coordinates (Xj,Yj) in the reference image is memorized (step 60), and the region similarity procedure relative to a specific significant point in the test image and a specific significant point in the reference image is terminated.

Conversely, in the event the normalized value is above the given threshold (NO output of step 59), a check is made (step 1) to determine whether the norm has been computed for all the possible positions of the significant point in the test image, bearing in mind the existing position tolerance (as explained above). This amounts to determining whether portions of the test image translated and centered about different pixels corresponding to various tolerance positions have been compared (unsuccessfully). In the event the comparison has not yet been made for all the different positions of the significant point (NO output of step 61), the method returns to step 56, which supplies further grey levels relative to a translated portion of the test image. Conversely (YES output of step 61), the possibility of a match between the two compared significant points is rejected, and the similarity procedure terminated.

The segment similarity procedure (described in detail below with reference to FIG. 5) is basically much the same as for the regions, and provides for "validating" a pair of significant points by determining the similarity of parts of the image interposed between the pair itself and the other pairs of significant points. Substantially, it comprises extracting the points lying in a segment joining a first and second significant point in the test image, and determining the similarity between this and a corresponding segment in the reference image. In this case also, similarity is computed as an integral norm $N_s$, here defined as a line integral as opposed to a double integral. Given the presence of discrete points, computing the integral norm $N_s$ amounts to calculating a single sum, again using flash cells, but this time only using a number of pairs of cells of array 40 (FIG. 3) equal to the number of points in the segments for comparison.

More specifically, to begin with, given a first significant point $P_0$ and second significant point $P_1$ in the test image, the points in a segment joining said two significant points are extracted (step 65) in any known manner (e.g., the points defining the shortest path between the two end points). Alternatively, other points may be taken along lines in the intermediate portion of the image between the two significant points (e.g., points along the sides of a square in said intermediate portion).

The length of the test segment so extracted and the length of the corresponding segment in the reference image are then normalized so that they are directly comparable (step 66); the grey levels of the points in the reference segment are memorized as programming voltages of pairs of cells 41 (step 67); the inputs of the same pairs of cells 41 are supplied with voltages proportional to the grey levels of the points in the test image segment (step 68); the value of the integral norm $N_s$ of the segment is read (step 69); and the value is normalized (step 70) and compared (step 71) with a predetermined threshold K3 (e.g., 0.18). If the value of $N_s$ is over K3, the segments are considered dissimilar (output NO of step 71) and the same procedure iks repeated for a different segment joining the same first considered significant point $P_0$ to a further significant point $P_2$ already established as matching going back to step 65.

Conversely (YES output of step 71), a counter L, initialized at the start of the segment similarity procedure for point $P_0$, is incremented (step 72); and a check is made to determine whether point $P_0$ has been compared with all the other established matching points $P_i$ (step 73). In the event of a negative response (NO output of step 73), the procedure continues with a comparison of the next points $P_i$ going back to step 65. In the event of a positive response in step 73, a check is made to determine whether the number of segments established as being similar for point $P_0$ is greater than or equal to a further threshold K4 (step 74). In the event of a negative response in step 74 (NO output), the segment similarity procedure relative to point $P_0$ is terminated without validating point $P_0$, owing to an insufficient similarity of the intermediate lines between point $P_0$ and the other matching significant points. Conversely, in the event of a positive response in step 74 (YES output), point $P_0$ is validated, a counter K for counting the number of validated matching significant points is incremented (step 75), and the procedure is terminated.

The advantages of the described method and device are as follows. In particular, they provide for fully automatic fingerprint identification of proven reliability (simulated tests recorded no false identification). Further, the hardware implementation, using flash cells, of the computationally longer functions provides for comparing even a large number of reference images within a reasonable length of time. Moreover, the practical implementation may easily be adapted, as required, to individual requirements, e.g., for satisfying the conditions of civilian security applications.

Clearly, changes may be made to the method and device as described and illustrated herein without, however, departing from the scope of the present invention. In particular, the operations described may be optimized in various ways; the flash cell array for computing the integral norm may be formed differently from that described, e.g., the pairs of cells 41 may be arranged in one line rather than in an array; and the integral norm may be computed by programming and reading the flash cells in the opposite way to that described, i.e., by programming the flash cells with the grey levels of the test image, and supplying the gate terminals with voltages proportional to the grey levels of the reference image.

What is claimed is:

1. A method of identifying fingerprints, the method comprising:

acquiring a test image comprising a number of test points characterized by a quantity related to a three-dimensional structure of the fingerprints, and defining a test surface;

determining significant points among said number of test points;

directly verifying a local region similarity between a test region surrounding one of said significant points and a corresponding reference region of a reference image comprising a number of reference points characterized by said quantity so as to define a reference surface, wherein said test and reference regions comprise a plurality of discrete points, wherein said verifying the local region similarity comprises computing an integral norm of portions of said test and reference surfaces by performing a double summation operation; and repeatedly verifying the local region similarity of a test region and a corresponding reference region for another of the significant points until all or a threshold amount of significant points have been verified;

wherein computing the integral norm is followed by:
comparing said integral norm with a second threshold value;

memorizing pairs of significant test and reference points for which said integral norm is below said second threshold value;

determining a rotation-translation such as to match two pairs of significant points;

calculating the number of pairs of matching significant points in said test image and said reference image with the rotation-translation determined;

comparing said number of pairs of matching significant points with a third threshold value; and determining the similarity of intermediate portions of said test and reference images between said pairs of matching significant points wherein determining the similarity of said intermediate portions comprises:
identifying a number of intermediate lines, each located in an intermediate region between a predetermined matching significant point in said test image and another matching significant point in said test image;

computing the integral norm of each of said lines;

comparing said integral norm of said lines with a fifth threshold value;

calculating a first numerical value correlated to the number of times said integral norm of a line is below said fifth threshold value;

comparing said first numerical value with a sixth threshold value; and validating said predetermined matching significant point if said first numerical value is at least equal to said sixth threshold value.

2. The method as claimed in claim 1, wherein computing the integral norm comprises programming flash cells with a threshold value correlated to a value of said quantity in said regions of the one of said test and reference images; biasing said flash cells with a voltage value correlated to a value of said quantity in said regions of the other of said test and reference images; and measuring the charge flowing through said flash cells.

3. The method as claimed in claim 2, wherein programming comprises programming a plurality of flash cells; said plurality of cells comprising pairs of flash cells equal in number to the test points forming one of the said test regions; said pairs of cells each being programmed with a first threshold value correlated to the value of said quantity at a respective reference point forming said respective reference region; and wherein biasing said flash cells comprises supplying gate terminals of each said pair of flash cells with a voltage correlated to the value of said quantity at a respective test point of the one of the said test regions.

4. The method as claimed in claim 3, wherein each pair of cells comprises a first and a second cell having source and drain terminals connected to each other and having respective gate terminals; wherein said first cell in a predetermined pair is programmed with a first threshold voltage proportional to said value of said quantity at said respective reference point, and said second cell in said predetermined pair is programmed with a second threshold voltage complementary to said first threshold voltage; and wherein said first cell in said predetermined pair is biased with an input voltage proportional to said value of said quantity at a respective test point, and said second cell in said predetermined pair is programmed with an input voltage complementary to said first input voltage.

5. The method as claimed in claim 1, wherein computing the integral norm is repeated a predetermined number of times for different portions of said test surface surrounding each significant test point.

6. The method as claimed in claim 1, wherein determining the similarity of said intermediate portions comprises extracting, from said test and reference images, points along lines lying in said intermediate portions; and computing the integral norm of said lines.

7. The method as claimed in claim 6, wherein extracting comprises extracting the points of segments connecting significant points in said pairs of significant points in said test image.

8. The method as claimed in claim 6, wherein computing the integral norm comprises programming flash cells with a fourth threshold value correlated to the value of said quantity at points along said lines of one of said test and reference images; biasing said flash cells with a voltage value correlated to the value of said quantity at points along said lines of the other of said test and reference images; and measuring the charge flowing through said flash cells.

9. The method as claimed in claim 1, further comprising repeating determining the similarity of said intermediate portions for all the matching significant points determined; calculating a second numerical value correlated to the number of validated matching significant points; comparing said second numerical value with a seventh threshold value; and confirming matching of said test and reference images in the event said second numerical value is above said seventh threshold value.

10. The method as claimed in claim 1, wherein said quantity comprises grey levels.

11. A method of identifying fingerprints, the method comprising:

acquiring a test image comprising a number of test points characterized by a quantity related to a three-dimensional structure of the fingerprints, and defining a test surface;

determining significant points among said number of points; and verifying a region similarity between test regions surrounding said significant points and corresponding reference regions of a reference image comprising a number of reference points characterized by said quantity so as to define a reference surface; wherein verifying the region similarity comprises:

computing an integral norm of portions of said test and reference surfaces, comparing said integral norm with a second threshold value, memorizing pairs of significant test and reference points for which said integral norm is below said second threshold value, determining a rotation-translation such as to match two pairs of significant points, calculating the number of pairs of matching significant points in said test image and said reference image with the rotation-translation determined, comparing said number of pairs of matching significant points with a third threshold value, and determining the similarity of intermediate portions of said test and reference images between said pairs of matching significant points by:

a) identifying a number of intermediate lines, each located in an intermediate region between a predetermined matching significant point in said test image and another matching significant point in said test image, b) computing an integral norm of each of said lines, c) comparing said integral norm of said lines with a fifth threshold value, d) calculating a first numerical value correlated to the number of times said integral norm of a line is below said fifth threshold value, e) comparing said first numerical value with a sixth threshold value, and f) validating said predetermined matching significant point if said first numerical value is at least equal to said sixth threshold value.

12. The method of claim 11 further comprising:

repeating said a)–f) for all the matching significant points determined;

calculating a second numerical value correlated to the number of validated matching significant points;

comparing said second numerical value with a seventh threshold value; and confirming matching of said test and reference images in the event said second numerical value is above said seventh threshold value.

13. The method of claim 1, further comprising defining an array of test image points as the test region surrounding one of said significant points and an array of reference image points as the corresponding reference region which surrounds a corresponding reference point, wherein computing the integral norm of portions of said test and reference surfaces includes computing an integral norm of the test and corresponding reference regions.

14. A method of identifying fingerprints, the method comprising:

acquiring a test image comprising a number of test points characterized by a quantity related to a three-dimensional structure of the fingerprints, and defining a test surface;

determining significant points among said number of test points;

directly verifying a local region similarity between a test region surrounding one of said significant points and a corresponding reference region of a reference image comprising a number of reference points characterized by said quantity so as to define a reference surface, wherein said test and reference regions comprise a plurality of discrete points, wherein said verifying the local region similarity comprises computing an integral norm of portions of said test and reference surfaces by performing a double summation operation;

repeatedly verifying the local region similarity of a test region and a corresponding reference region for another of the significant points until all or a threshold amount of significant points have been verified;

determining two matching pairs of significant points in said test image and said reference image; and determining the similarity of intermediate portions of said test and reference images between said pairs of matching significant points wherein determining the similarity of said intermediate portions comprises:

identifying a number of intermediate lines, each located in an intermediate region between a predetermined matching significant point in said test image and another matching significant point in said test image;

computing an integral norm of each of said lines;

comparing said integral norm of said lines with a fifth threshold value;

calculating a first numerical value correlated to the number of times said integral norm of a line is below said fifth threshold value;

comparing said first numerical value with a sixth threshold value; and validating said predetermined matching significant point if said first numerical value is at least equal to said sixth threshold value.

* * * * *